United States Patent [19]

Fock et al.

[11] Patent Number: 5,076,844
[45] Date of Patent: Dec. 31, 1991

[54] PERFLUOROALKYL GROUP-CONTAINING (METH-)ACRYLATE ESTERS, THEIR SYNTHESIS AND USE IN DENTAL TECHNOLOGY

[75] Inventors: Jürgen Fock, Düsseldorf; Günther Hahn, Mühlheim/Ruhr; Günter Wagerknecht, Echzell, all of Fed. Rep. of Germany

[73] Assignee: TH. Goldschmidt AG & GDF Gesellschaft für Dentale Forschung u. Innovationen GmbH, Rosbach, Fed. Rep. of Germany

[21] Appl. No.: 580,863

[22] Filed: Sep. 11, 1990

Related U.S. Application Data

[62] Division of Ser. No. 441,763, Nov. 27, 1989.

[51] Int. Cl.$^5$ ............................................. C09K 3/00
[52] U.S. Cl. ..................................... 106/35; 523/115
[58] Field of Search ............................................. 106/35

[56] References Cited

U.S. PATENT DOCUMENTS

| | | | |
|---|---|---|---|
| 3,469,317 | 9/1969 | Jarby et al. | 106/35 |
| 3,882,600 | 5/1975 | Plymale | 106/35 |
| 4,197,234 | 4/1980 | Temin | 524/502 |
| 4,515,910 | 5/1985 | Rawls et al. | 106/35 |
| 4,578,508 | 3/1986 | Griffith et al. | |
| 4,698,373 | 10/1987 | Tatesosian et al. | 522/10 |
| 4,920,188 | 4/1990 | Sakashita et al. | 526/196 |
| 4,957,985 | 9/1990 | Agou et al. | 523/106 |

FOREIGN PATENT DOCUMENTS 1178445  9/1985  U.S.S.R. .............................. 106/35

Primary Examiner—William R. Dixon, Jr.
Assistant Examiner—Sue Hollenbeck
Attorney, Agent, or Firm—Toren, McGeady & Associates

[57] ABSTRACT

Macromonomeric (meth-)acrylate esters, having fluoroalkyl groups are disclosed. The esters have the general formula

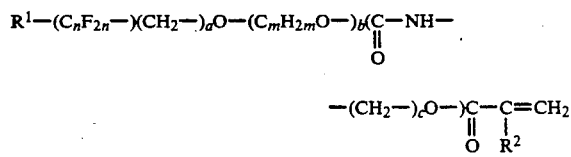

wherein
$R^1$ is the same or different and represents a hydrogen or fluorine group
$R^2$ is the same or different and represents a hydrogen or methyl group,
a has a value of 0, 1, 2, 3 or 4,
c has a value of 2, 3 or 4,
b has an average value of 2 to 30
n has an average value of 4 to 12 and
m has an average value of 3 to 14.

The products can be used in dentistry, preferably as relining material for dental prostheses. The esters have a lower solubility and a higher mechanical strength when cured and adhere to already cured poly(methyl methacrylate).

5 Claims, No Drawings

PERFLUOROALKYL GROUP-CONTAINING (METH-)ACRYLATE ESTERS, THEIR SYNTHESIS AND USE IN DENTAL TECHNOLOGY

This is a division of pending application Ser. No. 07/441,763 filed Nov. 27, 1989 pending.

FIELD OF THE INVENTION

The invention is directed to novel fluoroalkyl group-containing (meth)-acrylate esters, their synthesis as well as their use in dental technology. In particular, the invention is directed to such compounds, which are suitable as curable polymers in dentistry for relining dental prostheses.

The term "(meth-)acrylate esters" is intended to indicate that methacrylate esters, as well as acrylate esters are embraced by the invention.

BACKGROUND INFORMATION AND PRIOR ART

Fluorine-containing monomeric and oligomeric (meth-)acrylates are known from the literature. They are used for the production of dental prostheses and filling materials and endow them with reduced water absorption and lower solubility.

For example, the use of 1,1,5-trihydro-octafluoropentyl methacrylate as a polymerizable component of dental filling compositions is described in the J. Dent. Res. 58, 1181 to 1186. Moreover, fluorine-containing phenylcarbinol acrylates, such as 1,1,1,3,3,3-hexafluoro-2-phenyl-2-acryloyloxy-propane, are known from Org. Coat. Plast. Chem. 42, 204 to 207, 1980.

Furthermore, similar compounds and their use in dentistry are disclosed in U.S. Pat. No. 4,356,296. The U.S. Pat. No. 4,616,072 discloses perfluoroalkyl monomethacrylates as hydrophobic copolymers for dental filling materials. The monomers with substituted bis-phenyltetrafluoroethane, which are disclosed in the EP-A2-0 201 031 and 0 201 778 are likewise used in restorative dentistry.

These previously known monomers have the disadvantage that, as they cure, essentially hard, brittle polymers result. This greatly limits the possibility of their being used in dental technology.

OBJECT OF THE INVENTION

It is an object of the invention to provide curable monomers for use in dental technology which, aside from having a lower solubility and producing cured end products with a higher mechanical strength, can be used particularly as relining material for dental prostheses with increased adhesion to already cured poly(methyl methacrylate).

Generally, it is an object of the invention to improve on materials used in dentistry.

SUMMARY OF THE INVENTION

The novel, inventive macromonomeric fluoroalkyl groups-containing (meth-)acrylate esters have the general formula

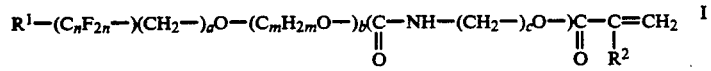

wherein $R^1$ is the same or different and represents a hydrogen or fluorine group $R^2$ is the same or different and represents a hydrogen or methyl group, a has a value of 0, 1, 2, 3 or 4, c has a value of 2, 3 or 4, b has an average value of 2 to 30 n has an average value of 4 to 12 and m has an average value of 3 to 14.

The above formula I is understood to be an average, general formula of a macromonomer mixture. The individual macromonomers differ particularly in the number of their oxyalkylene groups, which corresponds with the average value b as a maximum to a Schulz-Flory distribution or approximates such a distribution.

The chain length of the fluoroalkyl group is determined by the subscript n, which has an average value of 4 to 12. If the alcohol

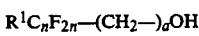

is a single compound, the value of n is absolute and corresponds to a whole number from 4 to 12. Preferred are compounds with an average or absolute value of $n = 6$ to $10$.

The hydroxyl function of the fluorinated alcohol may be separated from the perfluoroalkyl group by one or more $CH_2$ groups. The number of such $CH_2$ groups is determined by the value of a, which may be a whole number, namely 0, 1, 2, 3, or 4.

The subscript m of the oxyalkylene group $C_mH_{2m}O$— has an average value of 3 to 14. The oxyalkylene group may have the structure

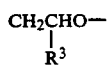

wherein $R^3$ is an alkyl group with 1 to 12 carbon atoms, or the structure $CH_2CH_2CH_2CH_2O$—, if tetrahydrofuran is used for the synthesis of the fluorinated alkanol polyether.

Examples of suitable oxyalkylene groups are the oxypropylene, oxybutylene, oxyoctylene, oxydecylene and oxydodecylene group. The inventive compounds may have the same or different oxyalkylene groups within the individual molecule, so that the subscript m is understood to be in the one case an absolute numerical value and, in the other, an average numerical value. If different oxyalkylene groups are present next to one another in the same molecule, whether arranged randomly (statistically) or in blocks, the molecule shall then be free of oxyethylene groups. If the molecule has only the same oxyalkylene groups, that is, if the value of m is understood to be absolute, it follows from the lower limit of $m = 3$ that oxyethylene groups are excluded.

Compounds, which contain perfluoroalkyl groups, are, as a rule, insoluble or not very soluble in conventional solvents and are for that reason difficult to handle.

Due to the presence of oxyalkylene groups with longer chain $R^3$ groups, the properties of the inventive compounds, especially after the polymerization, such as the hydrophobicity and the elastic/plastic behavior, as well as the solubility, can be influenced and adapted to the application.

The number of oxyalkylene groups is determined by the value of b and, on the average, is 2 to 30 and preferably 5 to 20.

Particularly preferred inventive compounds are those, in which in the average molecule at least 50 mole percent of the oxyalkylene units are oxypropylene and-/or oxybutylene units and the average value of m in the remaining oxyalkylene units it 5 to 14. It has been ascertained that these compounds are particularly suitable for the intended use.

Particularly preferred are compounds with the characteristic that, in the average molecule, at least 90 mole percent of the oxyalkylene units are oxypropylene and-/or oxybutylene units and the average value of m in the remaining oxyalkylene units is 5 to 14.

Compounds, in which the oxyalkylene units consist exclusively of oxypropylene and/or oxybutylene units, combine outstanding properties with low costs.

The alkoxylated perfluoroalkanols are synthesized advantageously by a cationic polyaddition reaction using Lewis acids, such as boron trifluoride, boron trifluoride etherate and tin tetrachloride.

A further aspect of the present invention is the method for the preparation of these compounds. This method is characterized in that a polyoxyalkylene monoether of the general formula

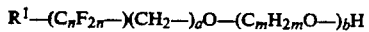

is reacted with an isocyanate of the general formula

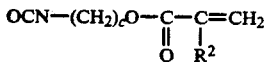

at temperatures ranging from 20° to 100° C., optionally in the presence of a solvent inert to isocyanate groups and optionally in the presence of a catalyst for the reaction of the isocyanate group with the hydroxyl group.

The subscripts of the above reactants have the meaning given above.

In general, the reaction takes place already at low temperatures, such as room temperature. Moderate warming to about 100° C. accelerates the course of the reaction. In most cases, it is possible to do without a solvent. If a solvent is desirable for process technical reasons, those solvents are suitable, which are inert to isocyanate groups, such as toluene or xylene. The use of a catalyst for the reaction of the isocyanate with the alcohol is advisable. Such catalysts are familiar to those skilled in the art and are described in the literature. Particularly preferred are tin catalysts, such as tin dibutyl dilaurate and tin octoate.

To avoid premature polymerization, a sufficient amount of a suitable polymerization inhibitor should be added to the reaction formulation. Suitable polymerization inhibitors are hydroquinone, hydroquinone monomethyl ether or t-butylcatechol.

The compounds obtained are distinguished, on the one hand, by their macromolecular character and, on the other, by their unsaturated terminal group, which, in turn, is capable of polymerizing. Such compounds are therefore also referred to a macromonomers in the art.

A further aspect of the invention is the use of the inventive compounds as curable monomers in dentistry. For this purpose, the inventive compounds are compounded with additives commonly used in dental technology. Such additives can be fillers, such as - particularly hydrophobized - glass-ceramics, finely divided silica or pigments or modifying agents. The function of the modifying agents is to optimize certain properties, which are important for the application, such as the elasticity, tear strength, ageing resistance and compatibility.

Further suitable modifying agents are divinylbenzene, ethylene glycol dimethacrylate, butanediol dimethacrylate, trimethylolpropane trimethacrylate and pentaerythritol tetramethacrylate.

Catalysts for the radiation-induced polymerization, such as benzil dimethyl ketal, 2,3-bornane dione, dimethylaminobenzenesulfanic acid bis(allyl amide), benzophenone and diethoxyacetophenone are furthermore added to the preparations in amounts of 0.1 to 3% by weight. The preparation is cured with the help of lights, which are normally used in dental technology and the radiation of which has a wave length of 200 to 550 nm.

The curing can also be carried out with peroxide catalysts or initiators at elevated temperatures. For this purpose, peroxides such as dibenzoyl peroxide are used. At low temperatures, cross linking with the help of redox initiators is possible. An example of such a redox initiator is the system of dibenzoyl peroxide/N,N-dihydroxyethyl-p-toluidine.

The compounding with various additives and the curing of the inventive (meth-)acrylate esters to dental products that are optimized for the particular application are accomplished in known fashion, the details of which may be taken, for example, from the publications cited above, particularly the EP-A2-0 201 031 and 0 201 778.

The invention is described in greater detail in the following Example, it being understood that this Example is given by way of illustration and not by way of limitation.

EXAMPLE (a) synthesis of an α-Hydroxy-ω-Perfluoroalkylalkanol Polyether (Not of the Invention)

Perfluorooctylethanol (170 g, approximately 0.37 moles) and 9.2 g of tin tetrachloride are heated in a pressure reactor under pure nitrogen to 60° C. Over a period of 3 hours, 163 g (approximately 2.8 moles) of propylene oxide are added. The contents of the reactor are reacted out during a further 0.5 hour at the same temperature. The reaction product is then cooled. The epoxide number of 0.01, determined on a sample of the product, indicates that the reaction has gone largely to completion. The product is neutralized with 25% by volume ammonia, the water is distilled off from it at 80° C. and 10 torr and, finally, it is filtered in the presence of a filter aid.

The hydroxyl number, determined by wet analysis, is 63. Assuming a functionality of 1, this hydroxyl number corresponding to a molecular weight of approximately 890.

b) Synthesis of an α-Methacryloyl-ω-Perfluoroalkanol Polyether Urethane (of the Invention)

The α-hydroxy-ω-perfluoroalkanol polyether from a) (445 g, approximately 0.5 moles) is mixed with 0.3 g of 2,6-di-tert.-butylcresol and heated to 45° to 50° C. While stirring constantly, 77.5 g (approximately 0.5 moles) of isocyanatoethyl methacrylate, to which one drop of tin dibutyl dilaurate had been added, is now added dropwise. The reaction temperature should not exceed 60° C. The course of the reaction is followed using an IR spectrophotometer until the NCO absorption bands have disappeared completely. The time required for this is about 12 hours, but can be shortened by the addition of tin(II) octoate. The yield is approximately 100%. The molecular weight, determined by osmometry, is 1040 and thus corresponds to the theoretically determined molecular weight.

c) Preparation of a Relining Material for Dental Prostheses, Which Remains Soft The inventive compound from b) (60 parts by weight) is mixed with 30 parts by weight of 2,2,3,3-tetrafluoropropyl methacrylate and 10 parts by weight of 2,2,3,3,4,4-hexafluoro-1,5-pentanediol dimethacrylate. Dibenzoyl peroxide (1.5% by weight) is added to the mixture.

Hydrophobic silica (35 parts by weight) is added to this solution with intensive mixing under vacuum in a laboratory planetary mixer. A clear, transparent paste results, which can be used by the press method as well as by the injection method as a soft relining material for dental prostheses. Curing takes place within 1 to 3 hours in the water bath at 70° to 90° C.

TABLE

| Example | Water Absorption mg/cm$^2$ | Shore A Hardness 37° C. |
|---|---|---|
| c) | 0.80 ± 0.20 | 30-35 |
| Commercial Product on Silicon Basis | 1.70 ± 0.80 | 30-35 |
| Commercial Product Based on Plasticized Methacrylate | 6.90 ± 1.20 | 47-50 |

We claim:

1. A dental preparation curable after application to dental work, said preparation comprising an effective amount of a macromonomeric (meth-)acrylate ester containing fluoroalkyl groups of the general formula $$R^1-(C_nF_{2n}-)(CH_2-)_aO-(C_mH_{2m}O-)_b(\underset{\underset{O}{\|}}{C}-NH-$$

$$-(CH_2-)_cO-)\underset{\underset{O}{\|}}{C}-\underset{\underset{R^2}{|}}{C}=CH_2$$

wherein
- $R^1$ is the same or different and represents a hydrogen or fluorine group
- $R^2$ is the same or different and represents a hydrogen or fluorine group
- $R^2$ is the same or different and represents a hydrogen or methyl group,
- a has a value of 0, 1, 2, 3 or 4,
- c has a value of 2, 3 or 4,
- b has an average value of 2 to 30
- n has an average value of 4 to 12 and
- m has an average value of 3 to 14.

2. A dental preparation as in claim 1, wherein in the average molecule of the macromonomeric ester at least 50 mole percent of the oxyalkylene units are oxypropylene and/or oxybutylene units and the average value of m for the remaining oxyalkylene units is 5 to 14.

3. A dental preparation as in claim 2, wherein in the average molecule of the macromonomeric ester at least 90 mole percent of the oxyalkylene units are oxypropylene and/or oxybutylene units and the average value of m for the remaining oxyalkylene units is 5 to 14.

4. A dental preparation as in claim 3, wherein the oxyalkylene units consist exclusively of oxypropylene and/or oxybutylene units.

5. The dental preparation of claim 1, in which n has an average or absolute value of 6 to 10.

* * * * *

UNITED STATES PATENT AND TRADEMARK OFFICE
CERTIFICATE OF CORRECTION

PATENT NO. : 5,076,844
DATED : December 31, 1991
INVENTOR(S) : Jürgen Fock, et al It is certified that error appears in the above-indentified patent and that said Letters Patent is hereby corrected as shown below:

On the title page, item

(75) Inventors : Jürgen Fock, Düsseldorf, Günther Hahn, Mühlheim/Ruhr, Günter Wagenknecht, Echzell, all Fed. Rep. of Germany Signed and Sealed this Twenty-sixth Day of October, 1993

Attest:

BRUCE LEHMAN

*Attesting Officer*  *Commissioner of Patents and Trademarks*